United States Patent
Maxfield

(10) Patent No.: US 10,758,677 B2
(45) Date of Patent: Sep. 1, 2020

(54) DRIVE MECHANISM

(71) Applicant: SHL MEDICAL AG, Zug (CH)

(72) Inventor: Brian Maxfield, Boca Raton, FL (US)

(73) Assignee: SHL MEDICAL AG, Zug (CH)

( * ) Notice: Subject to any disclaimer, the term of this patent is extended or adjusted under 35 U.S.C. 154(b) by 150 days.

(21) Appl. No.: 15/564,123

(22) PCT Filed: Mar. 23, 2016

(86) PCT No.: PCT/EP2016/056384
§ 371 (c)(1),
(2) Date: Oct. 3, 2017

(87) PCT Pub. No.: WO2016/169719
PCT Pub. Date: Oct. 27, 2016

(65) Prior Publication Data
US 2018/0078703 A1 Mar. 22, 2018

(30) Foreign Application Priority Data
Apr. 24, 2015 (SE) ...................................... 1550497

(51) Int. Cl.
*A61M 5/20* (2006.01)
*A61M 5/315* (2006.01)
(Continued)

(52) U.S. Cl.
CPC ...... *A61M 5/2033* (2013.01); *A61M 5/31505* (2013.01); *A61M 5/3202* (2013.01);
(Continued)

(58) Field of Classification Search
CPC .. A61M 5/20; A61M 5/2033; A61M 5/31566; A61M 5/3157; A61M 5/31565;
(Continued)

(56) References Cited

U.S. PATENT DOCUMENTS 4,642,099 A * 2/1987 Phillips ................. A61M 5/204
604/136
5,279,586 A * 1/1994 Balkwill ............. A61M 5/3158
222/309

(Continued)

FOREIGN PATENT DOCUMENTS

CA 2895586 A1 * 6/2014
CA 2897351 A1 * 7/2014 .......... A61M 5/2033

(Continued)

*Primary Examiner* — Nathan R Price
*Assistant Examiner* — Mark A Igel
(74) *Attorney, Agent, or Firm* — McDonnell Boehnen Hulbert & Berghoff LLP

(57) ABSTRACT

The present invention relates to a drive mechanism for a medicament delivery device, comprising a plunger rod (54) arranged to act on a stopper (28) arranged in a medicament container (16); a compression drive spring (58) operably connected to said plunger rod (54) and capable of applying a force on said plunger rod (54); a spring guide (78) arranged coaxial with, and radially outside, said compression drive spring (58), capable of preventing buckling of said drive spring, wherein said spring guide (78) comprises a resilient force element (86) capable of applying a force on said medicament container (16).

20 Claims, 7 Drawing Sheets

(51) Int. Cl.
*A61M 5/24* (2006.01)
*A61M 5/32* (2006.01)

(52) U.S. Cl.
CPC ............... *A61M 2005/2013* (2013.01); *A61M 2005/2073* (2013.01); *A61M 2005/2477* (2013.01); *A61M 2207/00* (2013.01)

(58) Field of Classification Search
CPC ............... A61M 5/31; A61M 5/31541; A61M 5/31533; A61M 5/31535; A61M 2005/2013; A61M 2005/2073; A61M 2005/2477; A61M 5/31505; A61M 5/3202
See application file for complete search history.

(56) References Cited

U.S. PATENT DOCUMENTS

| | | | | |
|---|---|---|---|---|
| 5,300,030 | A | * | 4/1994 | Crossman ........... A61M 5/2033 604/134 |
| 5,425,715 | A | * | 6/1995 | Dalling ............... A61M 5/2033 604/135 |
| 5,921,966 | A | * | 7/1999 | Bendek ................ A61M 5/24 604/207 |
| 6,099,503 | A | * | 8/2000 | Stradella ............. A61M 5/2033 604/131 |
| 7,749,195 | B2 | * | 7/2010 | Hommann .......... A61M 5/2033 604/135 |
| 7,806,866 | B2 | * | 10/2010 | Hommann .......... A61M 5/2033 604/136 |
| 2001/0005781 | A1 | * | 6/2001 | Bergens .............. A61M 5/2033 604/208 |
| 2007/0021718 | A1 | * | 1/2007 | Burren ................. A61M 5/24 604/110 |
| 2008/0147006 | A1 | | 6/2008 | Brunnberg et al. |
| 2010/0049125 | A1 | * | 2/2010 | James ................ A61M 5/2033 604/110 |
| 2010/0152659 | A1 | * | 6/2010 | Streit ................. A61M 5/2033 604/136 |
| 2012/0220954 | A1 | * | 8/2012 | Cowe ................. A61M 5/2033 604/228 |
| 2013/0190721 | A1 | * | 7/2013 | Kemp ................ A61M 5/2033 604/506 |
| 2013/0190722 | A1 | * | 7/2013 | Kemp ................ A61M 5/2033 604/506 |
| 2014/0046259 | A1 | * | 2/2014 | Reber ................ A61M 5/2033 604/136 |
| 2014/0107587 | A1 | * | 4/2014 | Hogdahl ............ A61M 5/2033 604/228 |
| 2016/0082190 | A1 | * | 3/2016 | Karlsson ............ A61M 5/2033 604/220 |
| 2017/0080153 | A1 | * | 3/2017 | Maxfield ........... A61M 5/31576 |
| 2018/0256820 | A1 | * | 9/2018 | Schader ............. A61M 5/2466 |

FOREIGN PATENT DOCUMENTS

| | | | |
|---|---|---|---|
| CN | 1933864 A | 3/2007 | |
| CN | 101072595 A | 11/2007 | |
| CN | 101124005 A | 2/2008 | |
| CN | 102202712 A | 9/2011 | |
| CN | 103370091 A | 10/2013 | |
| CN | 103547304 A | 1/2014 | |
| CN | 105555338 A | 1/2014 | |
| WO | 2006062788 A2 | 6/2006 | |
| WO | WO-2006062788 A2 * | 6/2006 | ........ A61M 5/2033 |
| WO | WO-2011053225 A1 * | 5/2011 | ........ A61M 5/2033 |
| WO | WO-2011133089 A1 * | 10/2011 | ............ A61M 5/20 |
| WO | 2012070035 A1 | 5/2012 | |
| WO | 2013032389 A1 | 3/2013 | |
| WO | WO-2013178512 A1 * | 12/2013 | |
| WO | WO2014159017 A1 | 10/2014 | |

* cited by examiner

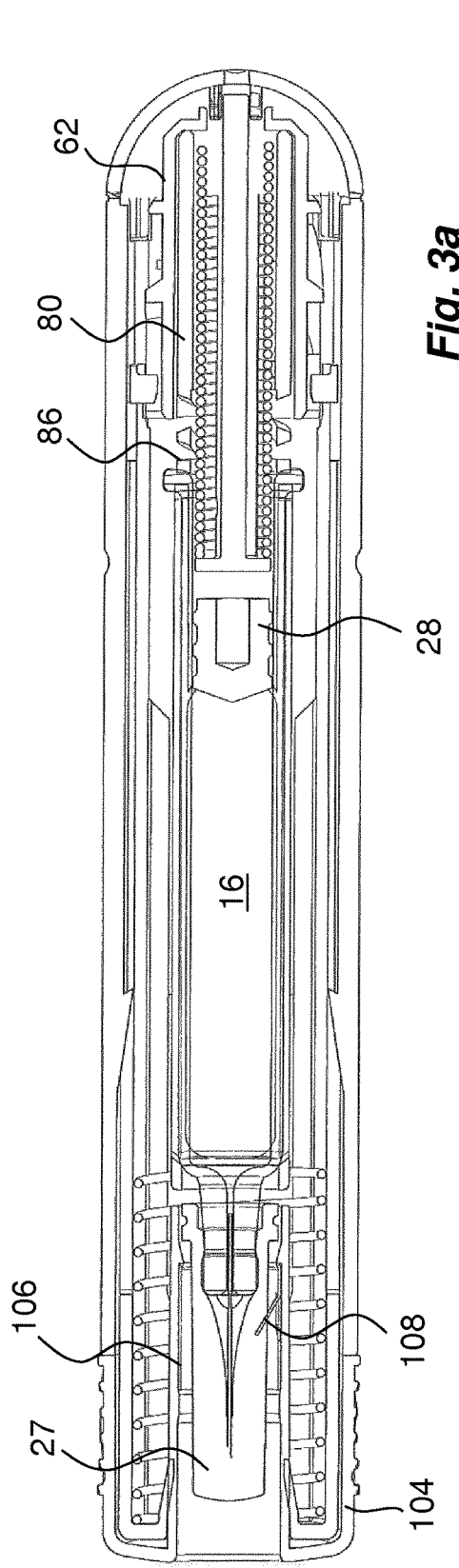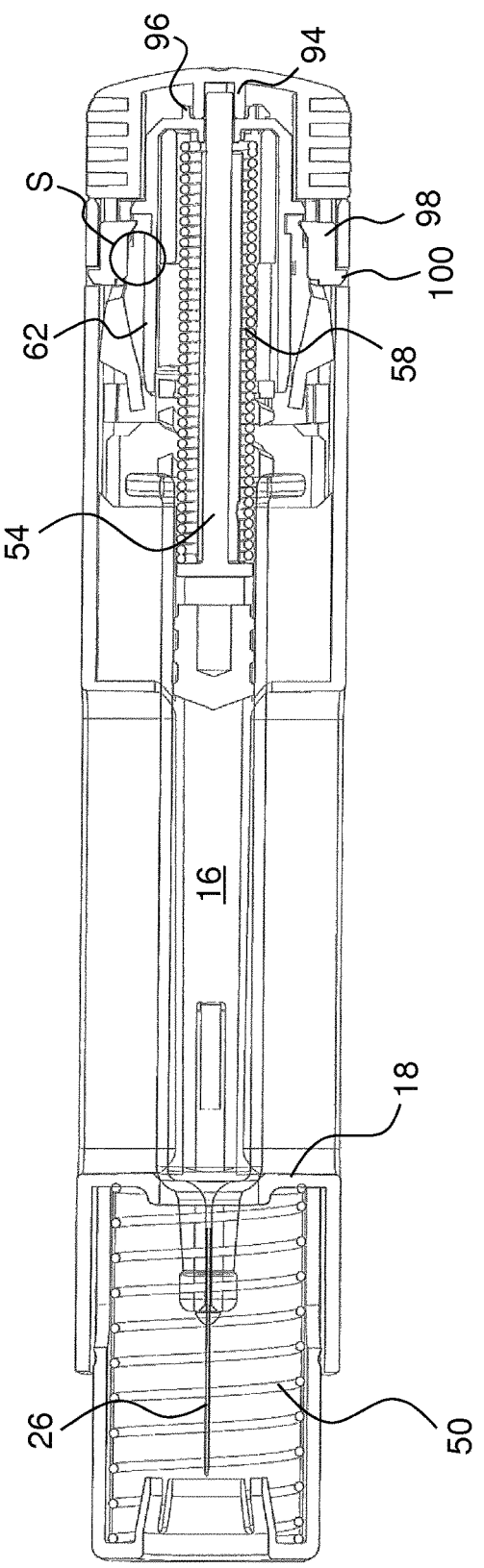
Fig. 3a
Fig. 3b

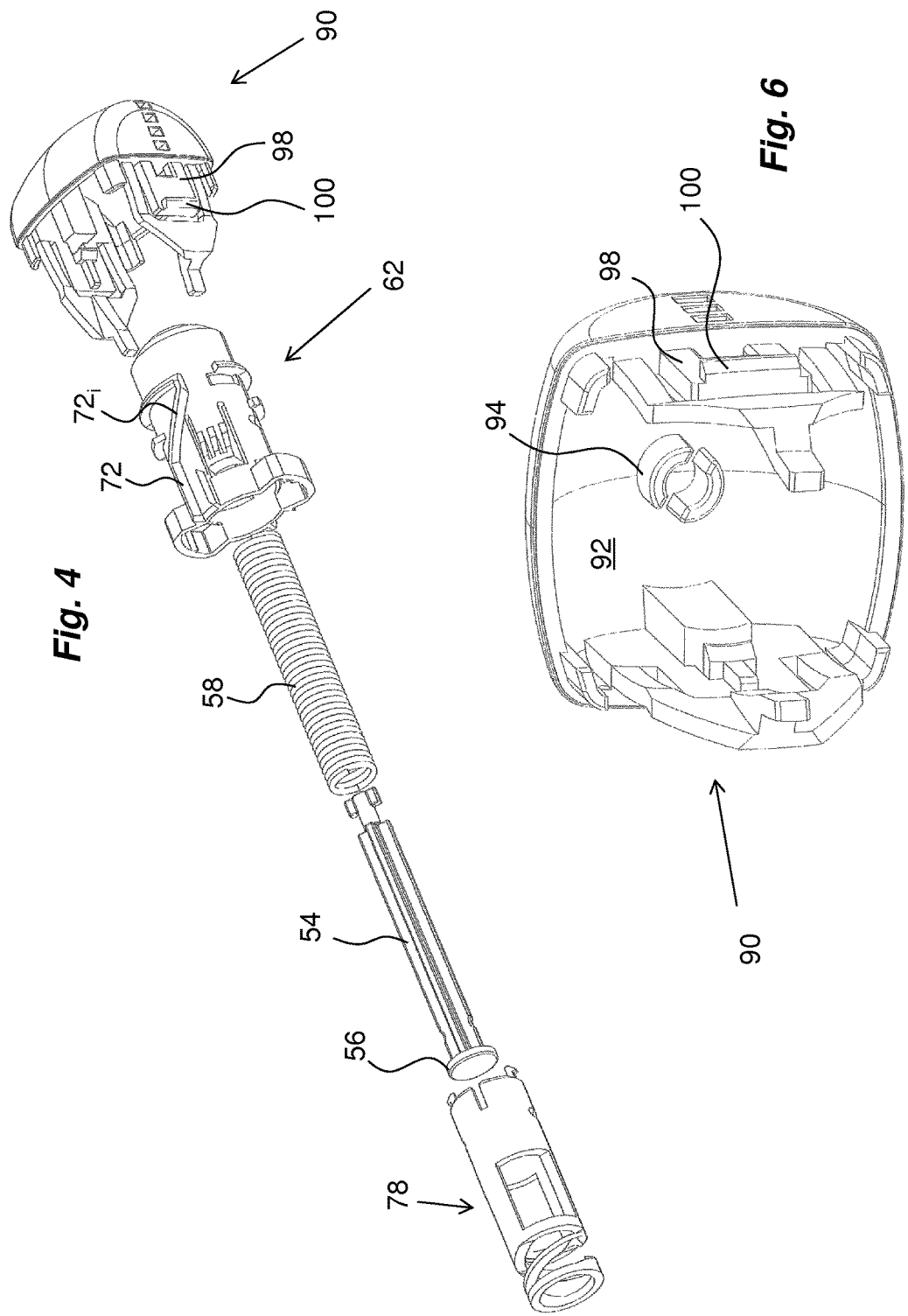

DRIVE MECHANISM

CROSS REFERENCE TO RELATED APPLICATIONS

The present application is a U.S. National Phase Application pursuant to 35 U.S.C. § 371 of International Application No. PCT/EP2016/056384 filed Mar. 23, 2016, which claims priority to Swedish Patent Application No. 1550497-0 filed Apr. 24, 2015. The entire disclosure contents of these applications are hereby incorporated by reference into the present application.

TECHNICAL AREA

The present invention relates to a drive mechanism to be used with a medicament delivery device, and in particular a drive mechanism arranged with a compression spring.

BACKGROUND OF INVENTION

A number of medicament delivery devices have been developed wherein a medicament container is placed inside the housing of the devices. The medicament container has to be supported in an appropriate manner in order to minimize the risk of breakage, which is a pronounced risk when the containers often are made of glass and wherein the force of a power pack, comprising a compression spring, often provide strong forces.

On the other hand, due to manufacturing aspects, as few components as possible are favoured, especially for disposable medicament delivery devices in order to keep the costs as low as possible.

With these aspects in mind some developments have been made. For instance the document US 2007/0021718 discloses the use of a compression spring for elastically supporting a medicament container in place in a housing of a medicament delivery device. The spring may be positioned between a distal end surface of the medicament container and an insert which is secured axially in the housing. The spring is preferably made of a plastic material.

Further, often when compression springs are used, some sort of support is required for preventing buckling of the spring. One common solution is then to have a guide rod extending inside the compression spring, such as is disclosed for example in WO 2013/032389. Another solution is to have a hollow plunger rod that is extra long and to place the compression spring inside the plunger rod.

A drawback with the use of a guide rod is that an extra component is needed, which component is not optimal from an assembly point of view of a power unit, because it has to be attached to a distal end wall of the medicament delivery device. On the other hand, the use of very long plunger rods is not optimal from a design point of view because the medicament delivery devices become long and not very attractive for an end user.

BRIEF DESCRIPTION OF INVENTION

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present invention is to remedy the drawbacks of the state of the art devices. This aim is obtained by a drive mechanism having the features of the independent patent claim. Preferable embodiments of the invention form the subject matter of the dependent patent claims.

The present invention relates to a drive mechanism for a medicament delivery device that comprises a plunger rod arranged to act on a stopper arranged in a medicament container. The drive mechanism also comprises a compression drive spring operably connected to the plunger rod and capable of applying a force on the plunger rod. Further a spring guide member is arranged coaxial with, and radially outside, the compression drive spring, capable of preventing buckling of the drive spring. In this manner the spring guide member will very effectively keep the compression drive spring straight even when it is held in a tensioned state, while not making the medicament delivery device unnecessarily long.

The spring guide member has a further feature in that it may comprise a resilient force element capable of applying a force on the medicament container. The force element will then aid in holding the medicament container in place in a medicament delivery device.

In order to function well as a guide for the drive spring, the spring guide may comprise a tubular body extending along a length of said compression drive spring. The design provides extended guide surfaces inside the tubular body. Preferably the compression spring is arranged coaxially with and radially outside the plunger rod. This provides a somewhat different solution than is normally used where the drive spring is positioned inside a hollow plunger rod and wherein a thin guide rod is placed inside the drive spring.

According to a preferred solution, the resilient force element may comprise a spring guide member spring arranged between a proximally directed surface of said spring guide and a distally directed surface of the medicament container. With this solution, the spring guide member spring may be arranged coaxial with, and radially outside the compression drive spring. Then, in order for the springs not to be engaged with each other, the spring guide member spring may have a winding direction that is opposite the winding direction of the compression drive spring.

The drive mechanism is preferably used in a medicament delivery device comprising a housing, which housing is arranged to accommodate said drive mechanism and said medicament container.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 3 is a cross-sectional view of the medicament delivery device according to FIG. 1, FIGS. 4-9 are detailed views of components of the present invention.

DETAILED DESCRIPTION OF THE INVENTION

Figure 2B:
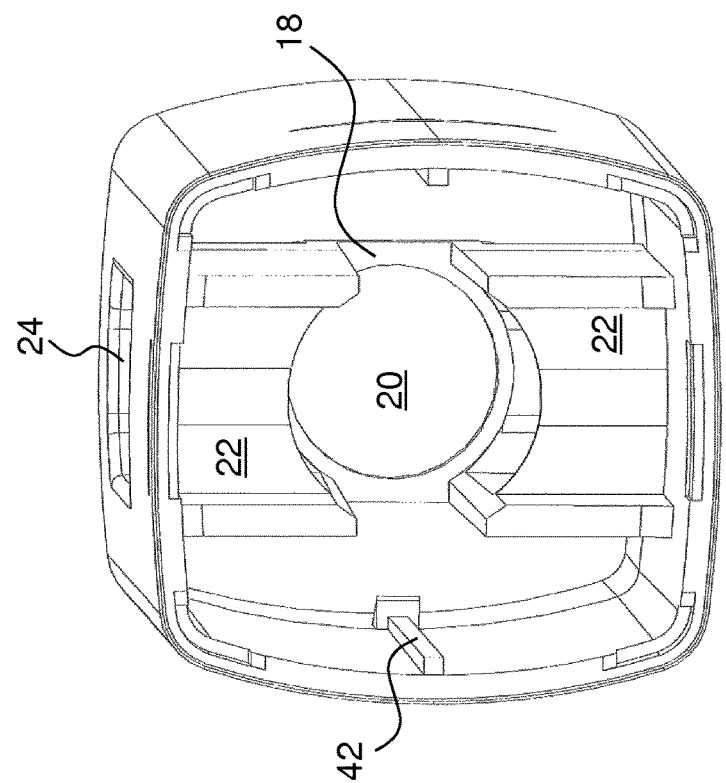
FIG. 2 is a detailed view of a housing comprised in the medicament delivery device of FIG. 1.
Figure 2A:
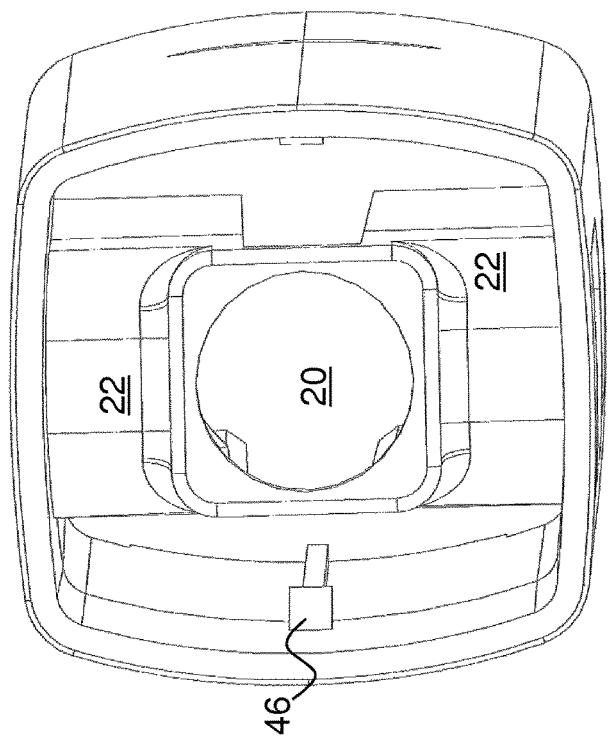

The embodiment shown of a medicament delivery device comprises a generally elongated housing 10 having a proximal end 12 and a distal end 14. The housing 10 is further arranged to accommodate a medicament container 16. Thereby a support surface 18, FIG. 2, is arranged with a central passage 20 through which a proximal end of the medicament container 16 may protrude and wherein a neck portion of the medicament container 16 may rest as seen in FIG. 3b, providing a stop surface in the proximal direction. The support surface 18 is an integral part of wall elements 22 surrounding openings or windows 24 in the housing. The wall elements 22 further act as supports for the medicament container 16 in the transversal directions. The medicament container 16 is arranged with a suitable medicament delivery member 26 that in the embodiment shown is an integrated injection needle. It is however to be under-stood that other types of medicament delivery members may be used such as attach-able injection needles, wherein different types of attachment elements may be utilized such as screw threads, bayonet fittings, luer connections, etc. The medicament delivery member is preferably protected before use by a medicament delivery member shield 27, in the embodiment shown, a so called rigid needle shield or RNS. It is however to be understood that other types of medicament delivery member shields may be used in order to obtain the desired protection of the medicament delivery member. The medicament container is further arranged with a movable stopper 28.

The proximal end 12 of the housing is arranged with a central passage 30. A medicament delivery member guard 32 is arranged to fit into the central passage 30 and to be movable in the longitudinal direction. The medicament delivery member guard 32 is arranged with a proximal end wall 34 having a central passage 36.

medicament delivery member guard 32 is further arranged with two distally directed arms 38 that run along inner surfaces of the housing. Each arm 38 is arranged with a longitudinal groove 40, in which a guide ledge 42, FIG. 2b, arranged on the inner surface of the housing, may fit. Further, a longitudinal slit 44 is arranged on the arms 38, in which a stop ledge 46, FIG. 2a, may fit. At a distal end of the arms 38, inwardly directed protrusions 48 are arranged, the function of which will be explained. A medicament delivery member guard return spring 50 is further arranged between a proximally directed surface of the wall parts 22 and a distally directed surface of the end wall 34 of the medicament delivery member guard 32.

Figure 1:
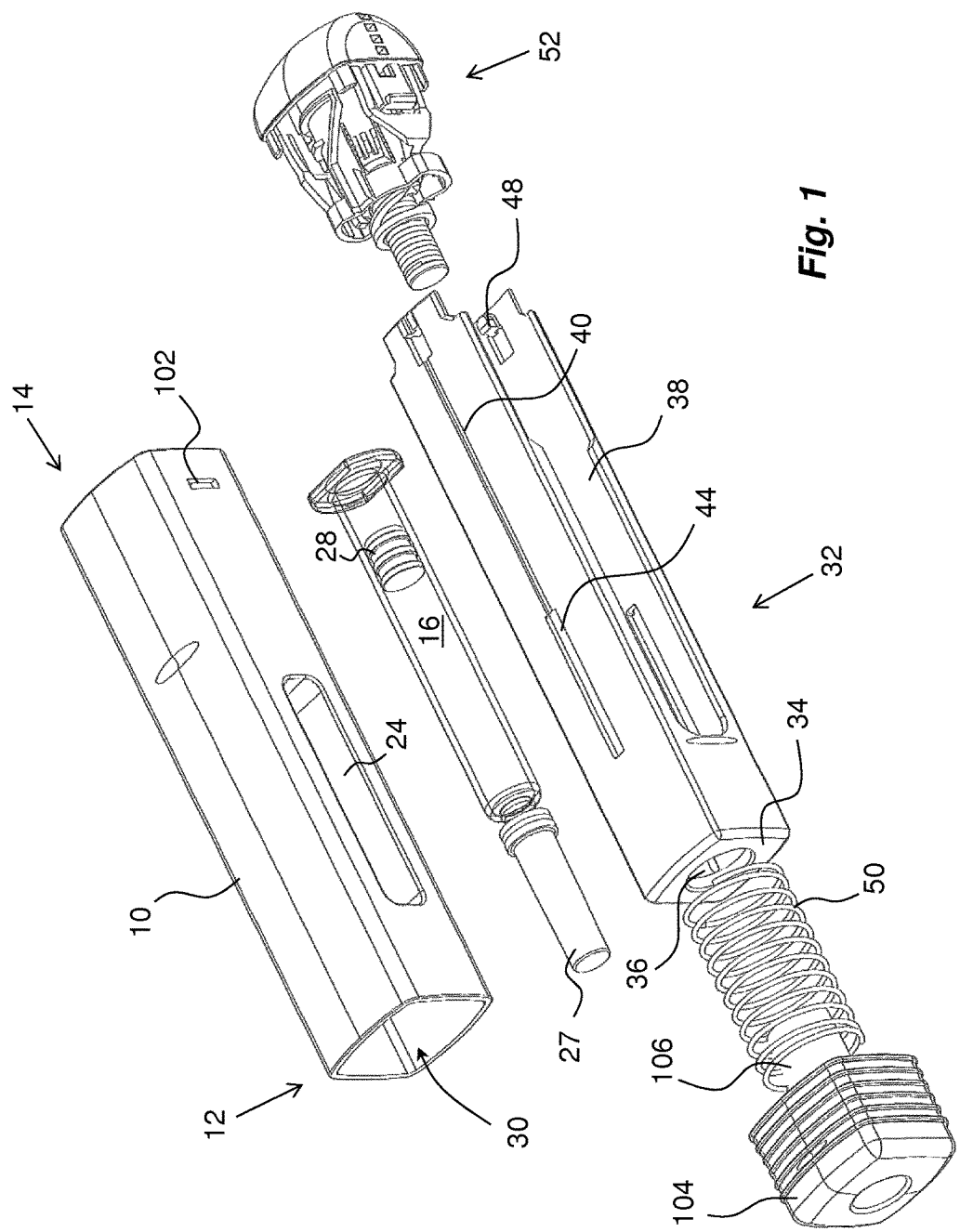
FIG. 1 is an exploded view of a medicament delivery device comprising a drive mechanism according to the present invention.
Figure 5:
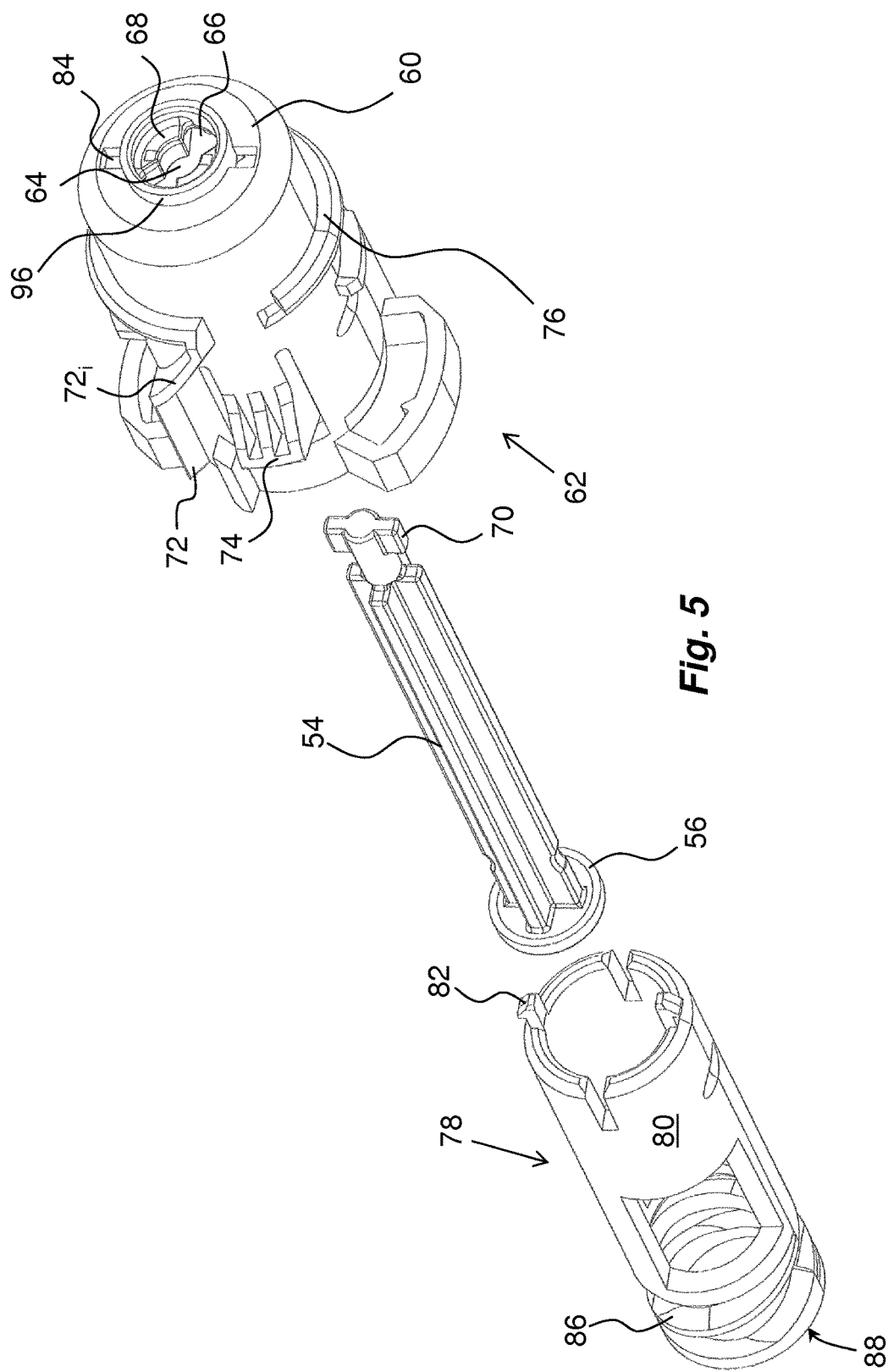
Figure 9:
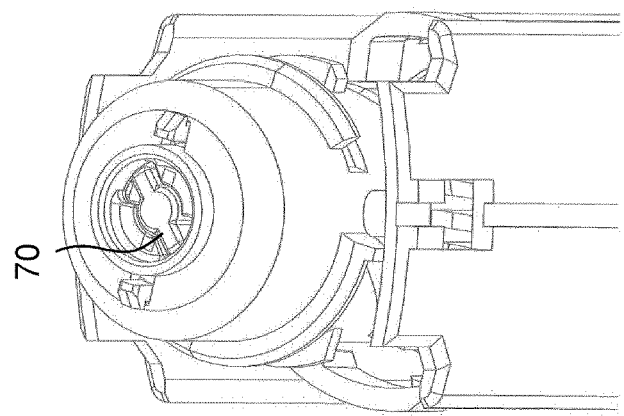

The medicament delivery device is further arranged with a power unit 52, FIGS. 1 and 5. It comprises a generally elongated plunger rod 54 provided with a disc 56 at its proximal end, which disc 56 has a diameter somewhat smaller than the inner diameter of the medicament container 16 and which disc 56 is to be in contact with the stopper 28 of the medicament container 16. The plunger rod 54 is surrounded by, and coaxial with, a compression drive spring 58 having its proximal end in contact with a distally directed surface of the disc 56 of the plunger rod 54, and with its distal end in contact with a proximally directed surface of an end wall 60 of a generally tubular rotator 62, FIG. 5.

The end wall 60 of the rotator 62 is arranged with a central passage 64 through which the plunger rod 54 may extend. The passage 64 is further arranged with cut-out sectors 66 with land sectors 68 in between. The plunger rod 54 is in that respect arranged with radially extending wings 70 at its distal end, which wings 70 fit into the cut-out sectors 66 and can rest on the distally directed surfaces of the land sectors 68, as will be described.

The rotator 62 is further arranged with guide ridges 72 that are intended to cooperate with the protrusions 48 of the medicament delivery member guard 32 as will be described, wherein some sections 72, of the guide ridges are inclined in relation to the longitudinal direction of the device. The rotator 62 is further arranged with wedge-shaped protrusions 74 arranged on generally radially flexible tongues, positioned adjacent the guide ridges 72, which wedge-shaped protrusions 74 are intended to lock the medicament delivery member guard 32 after completed use of the device as will be described. The rotator 62 is further arranged with blocking elements 76 that in the embodiment shown is designed as circumferentially extending ledges on the outer surface of the rotator 62, FIG. 5. The ledges 76 have a certain extension and position along the circumference, the function of which will be described below.

Figure 7:
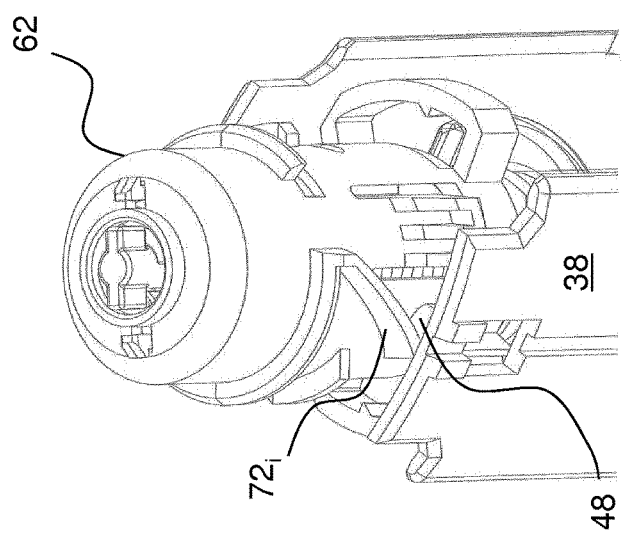

Positioned inside and coaxial with the rotator 62 is a spring guide 78, FIG. 5, having a generally tubular body part 80. A distal end surface of the body 80 is arranged with distally directed hooks 82, which are arranged to fit into passages 84 in the end wall 60 of the rotator 62, for attaching the spring guide 78 with the rotator 62. At the proximal end of the spring guide 78, a compression spring 86 is arranged, either attached to or made integral as seen in FIG. 7. The compression spring 86 is arranged with a ring-shaped end surface 88, which is intended to be in engagement with a distal end surface of the medicament container 16, urging the latter in the proximal direction against the seat 18 of the housing, as seen in FIG. 3.

The medicament delivery device further comprises an end cap 90, FIG. 6, to be attached to the distal end of the housing. The end cap 90 has a dome-shaped end wall 92 where its proximally directed inner surface is arranged with two arc-shaped proximally extending protrusions 94 arranged such that the distal end of the plunger rod 54 with its wings 70 will engage, whereby the plunger rod 54 is rotationally locked. The arc-shaped protrusions 94 also function as guide elements together with a distally directed annular protrusion 96 on the end wall 60 of the rotator 62, providing a journal support as will be described below. The end cap 90 is further arranged with two proximally directed arms 98. Each arm 98 is arranged with a generally radially outwardly extending ledge 100, where the ledges 100 are to engage in recesses 102, FIG. 1, at the distal end of the housing 10 for attachment of the end cap 90 with the housing.

Finally, the medicament delivery device is arranged with a safety cap 104, FIGS. 1 and 3a. It comprises a generally tubular grip body designed to fit onto the proximal end of the medicament delivery device with a friction fit with the medicament delivery member guard 32. A generally tubular medicament delivery member shield remover 106 extends into the central passage of the medicament delivery member guard 32 and surrounds the medicament delivery member shield 27. The medicament delivery member shield remover 106 is arranged with proximally directed inclined tongues 108 that engage with the outer surface of the medicament delivery member shield 27 to grip it.

The device is intended to function as follows. Before delivered to a user, the end cap 90 is not yet attached and a medicament container 16 is entered into the housing 10 from the distal end 14. Thereafter the power unit 52 is placed inside the housing 10. The compression drive spring 58 is in a tensioned state with the plunger rod 54 held in place in relation to the rotator by the wings 70 engaging the land sectors 68. The end cap 90 is attached by pushing it in the proximal direction into the distal passage of the housing 10. The arms 98 of the end cap 90 will flex inwards when the outwardly directed ledges 100 come in contact with the housing 10. They can flex inwards due to the space S between the inner surface of the housing 10 and the outer surface of the rotator 62 as seen in the circle of FIG. 3b. Finally the protective cap 104 is attached to the proximal end of the medicament delivery device. The medicament delivery device may now be delivered to a user.

Figure 8:
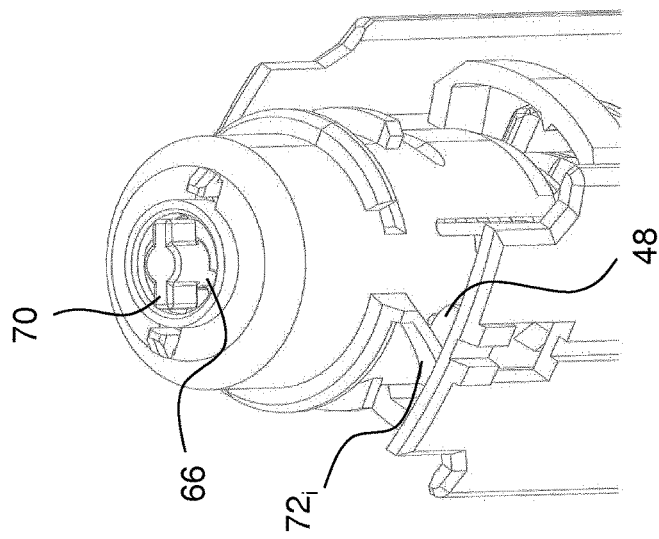

When a user is to administer a dose of medicament the protective cap 104 is pulled in the proximal direction. Due to the engagement of the medicament delivery member shield remover 106 with the medicament delivery member shield 27, it will be removed from the medicament delivery member 26. The next step is to press the proximal part of the medicament delivery device against a dose delivery site. This will cause the medicament delivery member guard 32 to be moved in the longitudinal direction in relation to the rest of the medicament delivery device, whereby a penetration of the medicament delivery member 26 is performed. The relative movement of the medicament delivery member guard 32 will cause the protrusions 48 to slide along the guide ridges 72 of the rotator 62 such that the protrusions 48 will come in contact with the inclined sections $72_i$ of the guide ridges, FIG. 7, which will cause the rotator 62 to turn around the longitudinal axis of the medicament delivery device, FIG. 8.

The turning of the rotator 62 will cause the cut-out sectors 66 of the passage 64 at the end wall 60 to move in relation to the wings 70 of the plunger rod 54, wherein the plunger rod 54 is prevented from turning due to the engagement with the arc-shaped protrusions 94 of the end cap 90.

Figure 10:
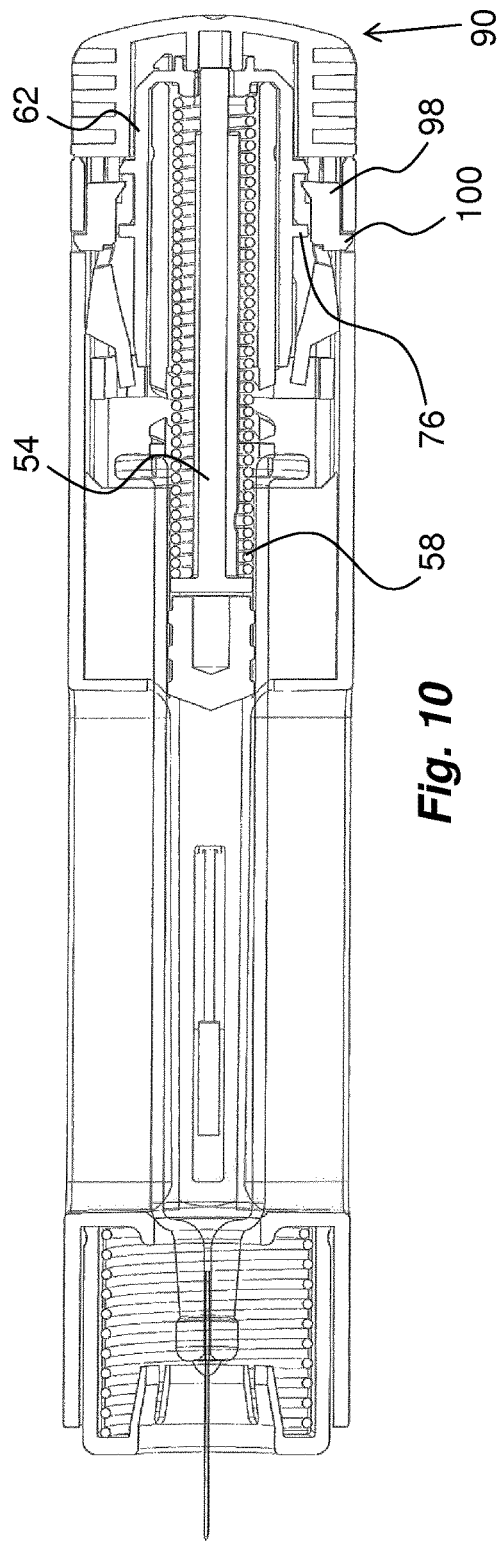
FIGS. 10-11 are cross-sectional views of different functional states of the medicament delivery device of FIG. 1.

Also, as the rotator 62 is turning, the stop ledges 76 on the outer surface of the rotator 62 are moved adjacent the free ends of the arms 98 of the end cap 90, as seen in FIG. 10. This action will prevent any movement in the radial direction of the arms 98. This aspect is important because when the rotator 62 has turned a certain rotational distance, the cut-out sectors 66 of the end wall 60 of the rotator 62 are aligned with the wings 70 of the plunger rod, whereby the plunger rod 54 is released, FIG. 10. When the plunger rod is released, so is the compression drive spring 58, which will urge the plunger rod 54 in the proximal direction. However, the drive spring 58 will also exert a force on the end wall 60 of the rotator 62, and thus on the end cap 90 because of the journalled connection of the rotator 62 with the end cap 90, and this force may cause the attachment of the end cap 90 to be disengaged. However, any disengagement is prevented by the stop elements 76 on the rotator 62 effectively preventing any movement of the arms 98.

Figure 11:
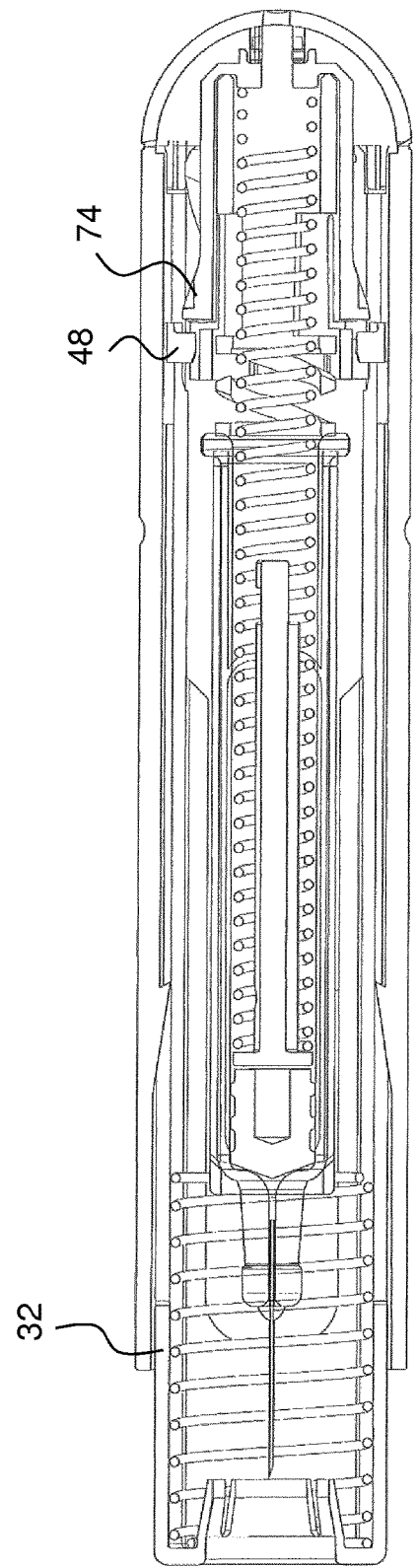

The movement of the plunger rod 54 in the proximal direction will cause it to move the stopper 28, whereby a delivery of a dose of medicament is performed through the medicament delivery member 26. When the dose has been delivered, the medicament delivery device may be removed from the dose delivery site. The medicament delivery member shield 32 will then be moved in the proximal direction by the force of the medicament delivery member shield spring 50, FIG. 11. The movement in the proximal direction of the medicament delivery member shield 32 will cause its protrusions 48 to move over the wedge-shaped protrusions 74 and be positioned proximal of the wedge 74, FIG. 11, thereby locking the medicament delivery member shield 32 in the extended position, thereby covering the medicament delivery member. The device may now be discarded.

It is to be understood that the embodiment described above and shown in the drawings is to be regarded only as a non-limiting example of the invention and that it may be modified in many ways within the scope of the patent claims.

The invention claimed is:

1. A drive mechanism for a medicament delivery device, comprising
   a plunger rod arranged to act on a stopper arranged in a medicament container;
   a compression drive spring operably connected to said plunger rod and configured to apply a first force on said plunger rod; and
   a spring guide arranged coaxial with, and radially outside, said compression drive spring,
   wherein the spring guide is configured to prevent buckling of said drive spring,
   wherein said spring guide comprises a tubular body and a resilient force element configured to apply an expansive second force between said medicament container and the tubular body.

2. The drive mechanism according to claim 1, the tubular body extending along a length of said compression drive spring.

3. The drive mechanism according to claim 1, wherein said compression drive spring is arranged coaxially with and radially outside said plunger rod.

4. The drive mechanism according to claim 1, wherein said resilient force element comprises a spring-guide spring arranged between a proximally facing surface of said tubular body and a distally facing surface of said medicament container.

5. The drive mechanism according to claim 4, wherein said spring-guide spring is arranged coaxial with, and radially outside said compression drive spring.

6. The drive mechanism according to claim 5, wherein said spring-guide spring has a winding direction that is opposite a winding direction of said compression drive spring.

7. The drive mechanism according to claim 1, wherein said resilient force element is integrated with the tubular body of the spring guide.

8. A medicament delivery device, comprising:
   a drive mechanism comprising:
      a plunger rod arranged to act on a stopper in a medicament container;
      a compression drive spring operably connected to said plunger rod and configured to apply a first force on said plunger rod, and
      a spring guide arranged coaxial with, and radially outside, said compression drive spring, wherein the spring guide is configured to prevent buckling of said compression drive spring, wherein said spring guide comprises a tubular body and a resilient force element configured to apply an expansive second force between said medicament container and the tubular body; and
   a housing arranged to accommodate said drive mechanism and said medicament container.

9. The medicament delivery device according to claim 8, the tubular body extending along a length of said compression drive spring.

10. The medicament delivery device according to claim 8, wherein said compression drive spring is arranged coaxially with and radially outside said plunger rod.

11. The medicament delivery device according to claim 8, wherein said resilient force element comprises a spring-guide spring arranged between a proximally facing surface of said tubular body and a distally facing surface of said medicament container.

12. The medicament delivery device according to claim 11, wherein said spring-guide spring is arranged coaxial with, and radially outside said compression drive spring.

13. The medicament delivery device according to claim 12, wherein said spring-guide spring has a winding direction that is opposite a winding direction of said compression drive spring.

14. The medicament delivery device according to claim 11, wherein the resilient force element is integrated with the tubular body of the spring guide.

15. The medicament delivery device according to claim 8, further comprising:
   a member guard in a central passage of the housing and moveable along a longitudinal axis; and
   a rotator coupled to the member guard, wherein the rotator axially retains the plunger rod in a distal position in the housing,
   wherein distal movement, along the longitudinal axis, of the member guard relative to the housing causes the rotator to rotate about the longitudinal axis, thereby releasing the plunger rod from the rotator such that the plunger rod moves proximally, relative to the housing, due to the first force applied to the plunger rod by the compression drive spring.

16. The medicament delivery device according to claim 15, wherein the rotator is coaxial with and radially outside the spring guide.

17. The medicament delivery device according to claim 15, wherein the rotator comprises a passage having a cross-sectional shape defined by one or more cutout sectors and one or more land sectors, and
   wherein a distal end of the plunger rod comprises one or more wings configured to: (i) engage the one or more land sectors when the plunger rod is in the distal position of the housing prior to rotation of the rotator, and (ii) pass through the one or more cutout sectors responsive to rotation of the rotator.

18. The medicament delivery device according to claim 17, further comprising a cap configured to prevent rotation of the plunger rod while the rotator rotates.

19. The medicament delivery device according to claim 15, wherein the spring guide is coupled to and rotationally fixed with the rotator.

20. The medicament delivery device according to claim 15, wherein a proximal end of the compression drive spring engages a portion of the plunger rod configured to engage the stopper of the medicament container, and
   wherein a distal end of the compression drive spring engages an end wall of the rotator.

* * * * *